United States Patent [19]

Corbett

[11] Patent Number: 4,607,955
[45] Date of Patent: Aug. 26, 1986

[54] STOCK CONSISTENCY TRANSMITTER

[75] Inventor: James O. Corbett, Eustis, Fla.

[73] Assignee: The Electron Machine Corporation, Umatilla, Fla.

[21] Appl. No.: 641,555

[22] Filed: Aug. 16, 1984

[51] Int. Cl.⁴ ............................................. G01N 21/53
[52] U.S. Cl. ..................................... 356/342; 162/49; 162/263; 250/564; 356/446
[58] Field of Search .................. 250/564, 574; 356/51, 356/342, 338, 442, 445, 446, 447, 448; 162/49, 263

[56] References Cited

U.S. PATENT DOCUMENTS

| 3,661,462 | 5/1972 | Natens | 356/51 |
| 3,962,581 | 6/1976 | Zimmerman | 356/51 X |
| 4,318,180 | 3/1982 | Lundqvist et al. | 162/49 X |

Primary Examiner—Vincent P. McGraw
Attorney, Agent, or Firm—Solon B. Kemon

[57] ABSTRACT

An electro-optical meter for indicating consistency of a liquid slurry, employs a light source and a detector of backscattered radiation. The light is caused to scan the slurry while holding the light intensity and the peak-to-peak value of the detected signal constant. The distribution of backscattered light is measured and the minimum to maximum intensity of backscattered light is controlled.

8 Claims, 5 Drawing Figures

STOCK CONSISTENCY TRANSMITTER

BACKGROUND OF THE INVENTION

Many manufacturing processes require continuous measurements of the consistency of a slurry being processed and a prime example is in the paper making art where the consistency of the aqueous fiber suspension must be monitored and controlled to ensure a uniform final product Electro-optical apparatus for this purpose is known and prior art examples may be found in U.S. Pat. Nos. 3,665,201, 3,990,795 and 4,040,743. The present invention relates generally to the broad class of apparatus shown in these patents and constitutes a significant improvement thereover in that the consistency readings are substantially independent of both ligth absorption by the liquid component of the slurry and the brightness of the suspended particulate matter.

BRIEF SUMMARY OF THE INVENTION

The present invention utilizes a collimated light scanning system for illuminating the slurry to be measured in combination with a detector of back scattered radiation from the particles in the slurry and appropriate signal processing circuitry connected to the ouptut of the detector to yield a continuous indication of slurry consistency which is independent of the brightness of the slurry particles and also independent of the absorption of the scanning light beam by the liquid portion of the slurry. This result is obtained by measuring distribution of back scattered light and controlling the minimum to maximum intensity of back scattered light.

DETAILED DESCRIPTION OF THE INVENTION

Figure 2:
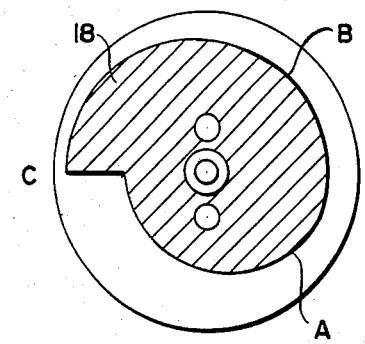
FIG. 2 is a plan view of the scanner disc of FIG. 1.
Figure 1:
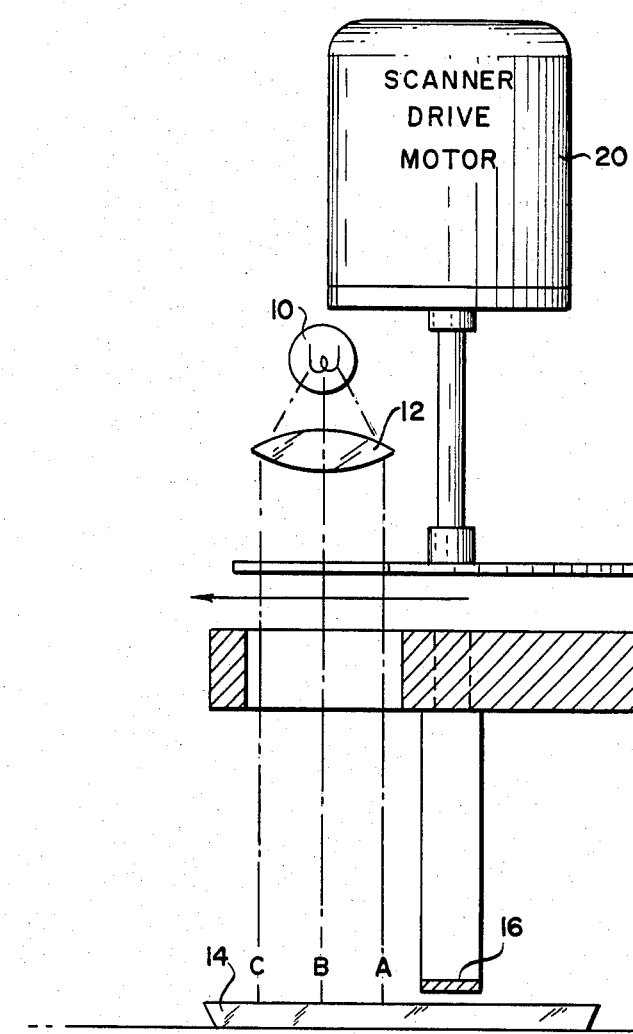
FIG. 1 is a diagrammatic side elevational view of the optical portion of the present invention.

The optical portion of the system shown diagrammatically in FIGS. 1 and 2 includes an incadescent lamp light source 10 and a collimating lens 12 for directing parallel light rays through a process window 14 to illuminate the stock which is moving by the window. A silicon light detector 16 is positioned adjacent the window at a location adjoining the illuminated area in order to detect back scattered radiation from the particles contained in the stock. In order to achieve cyclical repetitive movement between the light and the detector, a spiral scanner 18, shown in plan view in FIG. 2, is positioned between the lens 12 and the process window and is attached to the shaft of a drive motor 20. As the motor rotates, a collimated light beam moves in a straight line reciprocating path toward and away from the detector. The detector output is therefor a saw toothed AC wave as will be described with reference to FIGS. 4 and 5.

Figure 3:
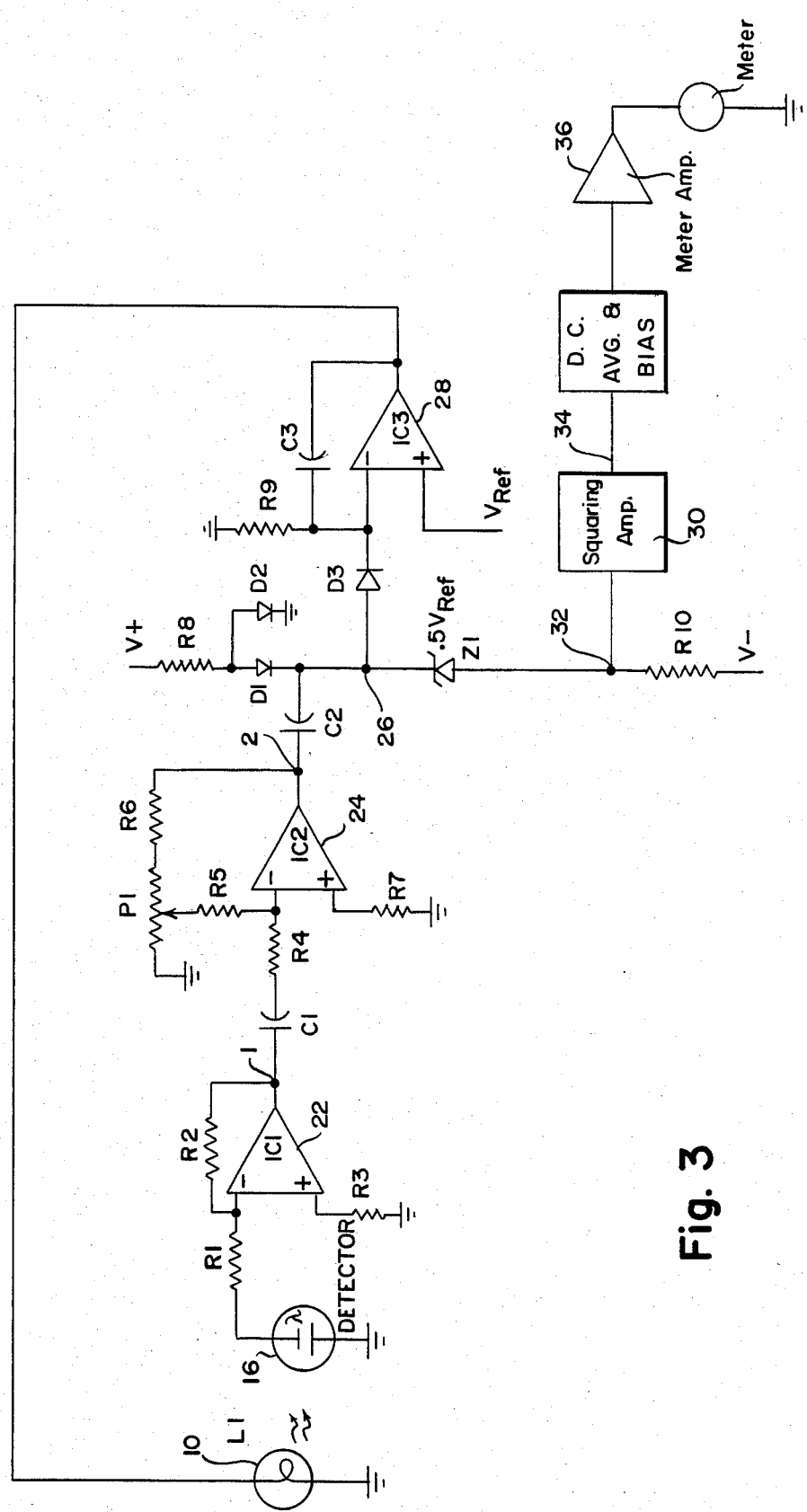
FIG. 3 is a schematic wiring diagram.

Referring now to the schematic wiring diagram of FIG. 3, for a description of the circuitry for controlling and processing the signal, the detector 16 is preferably a photovoltaic silicon detector, the output current of which is loaded by the resistor R1 to yield a substantially linear response for varying illumination levels. The output is connected to one input terminal of a preamp 22 which is an inverting amplifier to raise the signal level prior to feeding it to the cables which connect the sensing head to the remainder of the processing circuit. The capacitor C-1 in the output of the pre-amp decouples the signal so that only an alternating current signal will pass.

Amplifier 24 and its associated components P1, R6, R5, R4 and R7 form an inverting amplifier with adjustable gain. C2 which is in the output of amplifier 24 is a decoupling capacitor, again to block transmission of any DC component of the signal. Diodes D1 and D2 and R8 act as a clamp for holding the lower peak of the signal at ground potential as measured at terminal 26. Diode D3 is a peak detector and functions to rectify the AC saw tooth voltage and also charge capacitor C3. The third amplifier 28 functions as an automatic gain control amplifier to hold the illumination of the incandescent lamp 10 at a constant value. The voltage on the inverting input is compared with the voltage on the noninverting input and if the inverting input voltage is lower, the output of the amplifier starts integrating positively, increasing the voltage to the lamp and thus increasing the signal level until the voltage on the inverting input equals that of the non-inverting input. If the inverting input voltage is greater than the noninverting input, the output integrates negatively to reduce lamp intensity until the inputs are again equal. In this manner, the peak to peak saw tooth wave as measured at terminal 26 equals, the reference voltage applied to the non-inverting input. The potentiometer P1 in the feedback circuit of amplifier 24 can be adjusted to obtain the desired lamp voltage by modifying the loop gain. A fourth amplifier 30 functions as a squaring amplifier to square the signal as it changes polarity at terminal 32. The DC average and bias are: the DC average voltage of the square wave as measured at terminal 34 with the capability of adding bias to offset this average as desired to obtain the desired meter reading. The meter amplifier 36 has adjustable gain to increase meter deflection to obtain the desired meter span for the consistency of the stock being measured.

Figure 4:
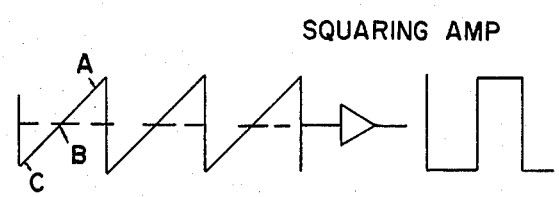
FIG. 4 shows the wave forms at the input and output of the squaring amplifier corresponding to a low consistency slurry.
Figure 5:
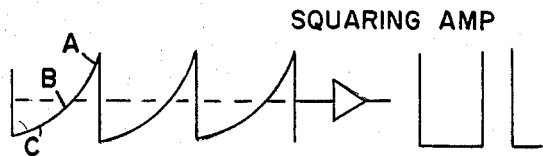
FIG. 5 shows the same wave forms as FIG. 4, but for a high consistency slurry.

Referring lastly to FIGS. 4 and 5, the saw tooth wave in FIG. 4 represents the output of the amplifier 22 and the letter designations A. B and C correspond to the position of the scanner member 18 of FIG. 2. The square wave to the right of the Figure represents the output of the amplifier 30 and in the case of 34 this would correspond to a low consistency stock. In FIG. 5, the same waves are shown corresponding to a high consistency stock and from that it can be seen that the ratio of the negative to the positive time of the square wave yields a result which is directly proportional to stock consistency.

While a preferred embodiment of the invention has been herein shown and described, applicant claims the benefit of a full range of equivalents within the scope of the appended claims.

I claim:

1. A method for electro-optically determining the consistency of a fibrous slurry, or other dispersed reflective suspension, the steps comprising:
   a. projecting a beam of light into the slurry;
   b. detecting with a photo-detector, light reflected from particles suspended in the slurry while causing cyclical repetitive relative movement between the detector and the light beam so that the electrical output of the detector is substantially a sawtooth AC voltage;

c. controlling the intensity of the light beam to hold the peak-to-peak value of said AC voltage constant;

d. converting said voltage to a square wave form, squaring at 50% of peak-to-peak value, and measuring the ratio of the time of positive to the time of negative portions of the square wave to derive a signal proportional to consistency and substantially independent of brightness of, material being measured and light absorption by the liquid portion of the slurry.

2. A method as defined by claim 1 in which the position of said detector is fixed and said light beam is caused to scan the slurry in a cyclical repetitive straight line pattern with respect to said detector.

3. A method as defined by claim 1 in which the slurry is moving by a measuring window.

4. A method as defined by claim 2 in which the slurry is moving by a measuring window.

5. Apparatus for electro-optically determining the consistency of a slurry comprising:

a. means for projecting a beam of light from a source into the slurry;

b. a photo-detector adjacent said means for detecting light reflected from particles suspended in the slurry;

c. scanning means for causing a cyclical repetitive movement between said detector and said light beam so that the electrical output of said photo-detector is a substantially sawtooth AC voltage;

d. control means interconnecting the output of said detector and said light source to hold the peak-to-peak value of said voltage constant;

e. means connected to convert said voltage to a square wave form, squaring at 50% of peak-to-peak value and;

f. means to measure the ratio of the positive to the negative times of said square wave to provide a signal proportional to said slurry consistency but independent of slurry brightness and light absorption by the liquid portion of the slurry.

6. Apparatus as defined by claim 5 in which said slurry is flowing past a transparent window and said first means and said photo-detector are positioned adjacent said window.

7. Apparatus as defined by claim 5 in which the position of said detector is fixed and said scanning means moves said light beam with respect to said detector.

8. Apparatus as defined by claim 6 in which the position of said detector is fixed and said scanning means moves said light beam with respect to said detector.

* * * * *